(12) United States Patent
Lotze et al.

(10) Patent No.: US 11,181,453 B2
(45) Date of Patent: Nov. 23, 2021

(54) APPARATUS FOR TESTING THE STRENGTH OF SHEETS MADE OF HARD BRITTLE MATERIAL UNDER TENSILE STRESS

(71) Applicant: SCHOTT AG, Mainz (DE)

(72) Inventors: Martin Lotze, Nieder-Olm (DE); Thomas Roßmeier, Bodenheim (DE); Clemens Ottermann, Hattersheim (DE); Volker Seibert, Hochheim (DE)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 16/740,564

(22) Filed: Jan. 13, 2020

(65) Prior Publication Data

US 2020/0150012 A1 May 14, 2020

Related U.S. Application Data

(62) Division of application No. 15/261,409, filed on Sep. 9, 2016, now Pat. No. 10,571,376.

(30) Foreign Application Priority Data

Sep. 11, 2015 (DE) .......................... 102015115345.9
Aug. 31, 2016 (DE) .......................... 102016116258.2

(51) Int. Cl.
*G01N 3/16* (2006.01)
*G01N 3/20* (2006.01)
*G01N 33/38* (2006.01)

(52) U.S. Cl.
CPC .............. *G01N 3/20* (2013.01); *G01N 33/386* (2013.01); *G01N 2203/0017* (2013.01); *G01N 2203/0248* (2013.01); *G01N 2203/0282* (2013.01)

(58) Field of Classification Search
CPC ........... G01L 5/10; G01L 5/107; G01L 5/106; G01N 33/346; G01N 3/10; G01N 3/20;
(Continued)

(56) References Cited

U.S. PATENT DOCUMENTS 4,346,601 A 8/1982 France
4,453,404 A 6/1984 Powell
(Continued)

FOREIGN PATENT DOCUMENTS

AT 411714 4/2004
DE 19540891 5/1996
(Continued)

*Primary Examiner* — Brandi N Hopkins
(74) *Attorney, Agent, or Firm* — Ohlandt, Greeley, Ruggiero & Perle, L.L.P.

(57) ABSTRACT

A method for testing the strength of a sheet-like element having two opposite faces and made of hard brittle material under tensile stress is provided. The method includes passing each of the faces of the element over a roller and thereby bending the element so that each of the faces is subjected to a first tensile stress in a portion in which the opposite face is in contact with a surface of the roller; exerting a second tensile force on the element in the direction of advancement so that both faces are subjected to the second tensile stress of at least 2 MPa so that the first and second tensile stresses add up to define a resultant tensile stress; and monitoring the element and determining whether the element has a defined breaking strength equal to the resultant tensile stress or whether the element breaks under the resultant tensile stress.

16 Claims, 5 Drawing Sheets

(58) Field of Classification Search
CPC ............. G01N 2203/0067; G01N 3/08; G01N 33/386; G01N 2203/0282; B32B 17/065; B32B 17/064; B32B 17/066; B65H 16/00; B65H 18/00; B65H 18/28; B65H 2301/4127; B65H 2301/5132; B65H 2801/61; C03B 13/04; H02N 13/00
See application file for complete search history.

(56) References Cited

U.S. PATENT DOCUMENTS

| | | | | |
|---|---|---|---|---|
| 5,101,661 | A * | 4/1992 | Cresson | G01L 5/10 73/159 |
| 5,182,722 | A * | 1/1993 | Hain | B07C 1/16 194/207 |
| 5,594,178 | A | 1/1997 | Takahashi | |
| 8,544,340 | B1 | 10/2013 | Ardelean | |
| 2008/0083288 | A1 | 4/2008 | Glaesemann | |
| 2013/0319048 | A1 | 12/2013 | Hartmann | |
| 2014/0060201 | A1 * | 3/2014 | Huang | G01N 3/08 73/826 |
| 2016/0033379 | A1 | 2/2016 | Heiss-Choquet | |
| 2016/0033380 | A1 | 2/2016 | Heiss-Choquet | |

FOREIGN PATENT DOCUMENTS

| | | |
|---|---|---|
| DE | 102012104594 | 12/2013 |
| DE | 102014110855 | 2/2016 |
| DE | 102014110856 | 2/2016 |
| JP | S6379061 | 4/1988 |
| JP | H10114537 | 5/1998 |
| JP | 2011202991 | 10/2011 |
| JP | 2013230964 | 11/2013 |
| JP | 2014002018 | 1/2014 |

* cited by examiner

APPARATUS FOR TESTING THE STRENGTH OF SHEETS MADE OF HARD BRITTLE MATERIAL UNDER TENSILE STRESS

CROSS REFERENCE TO RELATED APPLICATIONS

This application is a divisional of U.S. application Ser. No. 15/261,409 filed Sep. 9, 2016, which claims benefit under 35 USC § 119 of German Application 10 2015 115 345.9 filed Sep. 11, 2015 and German Application 10 2016 116 258.2 filed Aug. 31, 2016, the entire contents of all of which are incorporated herein by reference.

BACKGROUND

1. Field of the Invention

The invention generally relates to the testing of materials. More particularly the invention relates to an apparatus and a method for testing the breaking strength of sheets made of hard brittle material, in particular of glass.

2. Description of Related Art

Glass which is a hard brittle material exhibits a particular breaking behavior insofar as there is no predefined stress limit. Rather, fracture behavior is largely determined by statistical variables. Therefore, the strength of a glass ribbon can only be predicted in terms of a probability. In order to provide certainty as to what stress a certain piece of glass can resist the glass can be subjected to a specific stress. If the glass withstands this test it can be assumed that with a very high probability it will withstand a similar stress in the future.

Therefore, a strength test for testing all the produced glass may be envisaged for the purpose of quality assurance.

For this purpose, a method for proof testing a sheet of a brittle material is known from US 2008/0083288 A1, in which the sheet is bent and moved over a roller. Due to the bending, a tensile stress is exerted which corresponds to a predetermined strength value. U.S. Pat. No. 4,346,601 A discloses a similar arrangement with a plurality of rollers for proof testing glass fibers.

The method of US 2008/0083288 A1 is intended to identify sheets which have a strength greater than the predetermined strength value. However, a drawback of this approach is that the predetermined strength value is defined by the roller diameter and the glass thickness. It is not readily possible to test the material for an arbitrarily selectable tensile stress value. If the predetermined strength value is to be altered, a roller with a different diameter has to be chosen. Since usually both sides of the glass are to be tested, the glass has to be bent over at least two rollers in this case. Accordingly, two or more rollers have to be exchanged.

A phenomenon occurring upon breakage of hard brittle materials under tensile stress is known as stress corrosion cracking. If such a material, in particular glass, is exposed to permanent tensile stress, delayed fracture may be caused by stress corrosion cracking. In a proof test in which the glass is subjected to a mechanical stress for a very short time, stress corrosion cracking will possibly not have a sufficient effect so that possibly the glass withstands the proof test but then nevertheless breaks at a similar or even lower stress at a later time.

SUMMARY

The invention is therefore based on the object to improve strength testing of hard brittle materials such as in particular glasses, so that specific strength values to be tested can be predefined flexibly, and also to increase the reliability of such tests.

Accordingly, the invention provides a method for testing the strength of a sheet-like element having two opposite faces and made of hard brittle material, in particular glass. The element is tested for a predefined breaking strength under tensile stress. For this purpose, the element is passed over a roller at least once with each of the faces thereof and is bent thereby, so that each of the faces is subjected to a tensile stress in a portion in which the opposite face is in contact with a surface of the roller; and wherein a tensile force is exerted on the element in the direction of advancement so that both faces are subjected to a tensile stress of at least 2 MPa, preferably at least 5 MPa, more preferably at least 10 MPa; and this tensile stress and the tensile stress produced by the bending around the respective roller at the face facing away from the roller add up to define a resultant tensile stress, and the element is monitored for determining whether the element has a defined breaking strength equal to the resultant tensile stress or whether the element breaks under the resultant tensile stress applied.

This also allows to predetermine a minimum resistance of the element in the form of a tensile stress to which the element should resist and which is greater than the tensile stress caused by the bending of the element over the rollers. For testing, the tensile force that is exerted on the element in the advancement direction and corresponding to a tensile stress of at least 2 MPa is then set so that the resultant tensile stress is at least equal to the predefined tensile stress to which the element should resist.

A corresponding apparatus for testing such a sheet-like element made of hard brittle material for a predefined breaking strength under tensile stress comprises: transport means; and at least two rollers; wherein the transport means are adapted to pass the element over the rollers in a manner so that the element is bent and each of the faces is subjected to a tensile stress in a portion in which the opposite face is in contact with a roller surface; and further comprises pulling means for exerting a tensile force on the element in the direction of advancement, so that both faces of the element are subjected to a tensile stress of at least 2 MPa, preferably at least 5 MPa, more preferably at least 10 MPa; and this tensile stress and the tensile stress produced by the bending around the respective roller at the face facing away from the roller add up to define a resultant tensile stress; and wherein monitoring means are provided and adapted for monitoring the element and determining whether the element has a defined breaking strength equal to the resultant tensile stress or whether the element breaks under the resultant tensile stress applied.

The tensile stress additionally applied has two technical effects and advantages. With the invention, the tensile stress for which the material is to be tested can now be adjusted flexibly by adding a specific adjustable magnitude to the tensile stress predetermined by the roller radius. Another effect is that the additional tensile stress is permanently exerted during the test so that stress corrosion cracking may be initiated even already before the element runs over the rollers. This permits to better detect defective brittle-fracture elements, because the test is sensitive even to delayed fractures. The value of 2 MPa has proved useful to initiate crack growth at defects and to be able to reveal such defects with delayed fracture during the test.

One application of the invention is in-line testing of sheet-like glass elements during the manufacturing process which also includes hot forming. Therefore, according to one aspect of the invention a glass manufacturing system is provided which comprises a hot forming apparatus for forming a sheet-like glass article, in particular a glass ribbon, and an apparatus for testing according to the invention.

According to one embodiment, an element made of hard brittle material in the form of a glass ribbon is guided over the rollers and then wound up into a roll. Due to the examination of the glass for critical defects using the invention, the likelihood of breakage during storage of the glass ribbon in the form of a roll or during further processing is greatly reduced.

Furthermore, the invention is particularly suitable for testing thin glasses having a thickness of less than 0.4 millimeters. The invention is particularly preferably utilized for glass thicknesses of 100 µm and less. Just such thin glasses are often used for applications in which flexibility is important and which therefore are subjected to bending stress in use. However, glass thickness preferably is at least 5 µm.

BRIEF DESCRIPTION OF THE DRAWINGS

The invention will now be explained in more detail by way of further embodiments and with reference to the accompanying drawings. In the drawings in which like reference numerals designate the same or equivalent elements.

DETAILED DESCRIPTION

Figure 1:
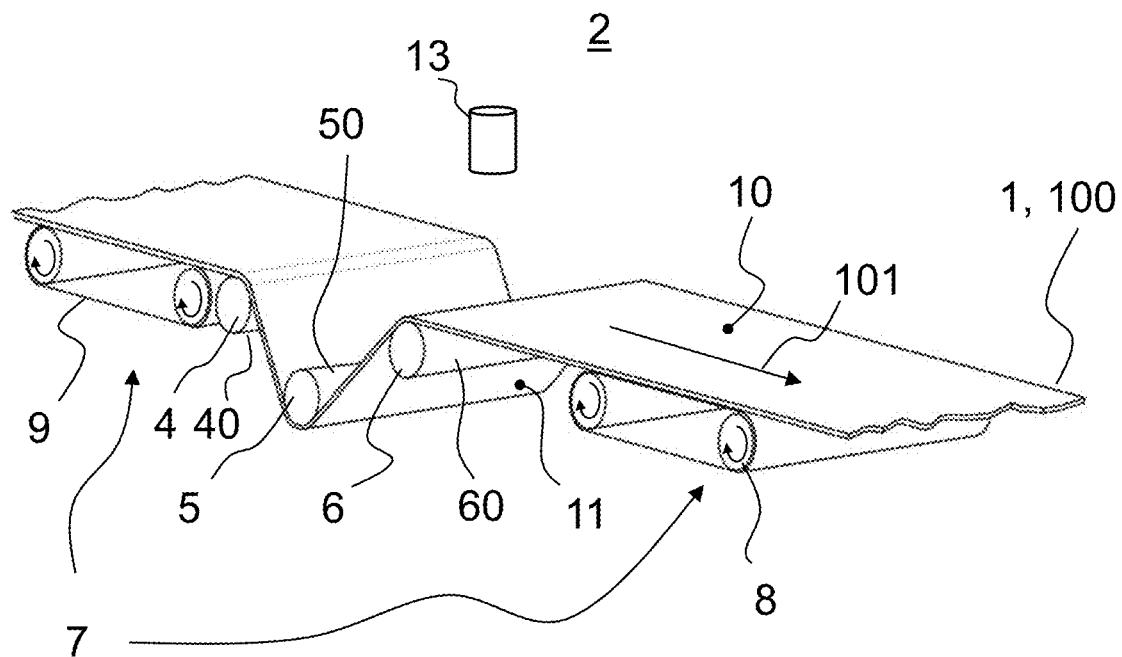
FIG. 1 shows parts of an apparatus for testing a sheet-like element made of hard brittle material.

FIG. 1 shows basic elements of an apparatus 2 of the invention for testing a sheet-like element 1 made of hard brittle material. Due to its sheet-like shape the element has two opposite faces 10, 11. Typically, these faces 10, 11 extend in parallel to each other. The two particularly flat faces 10, 11 are connected through edges or edge faces. Thus, the element 1 in particular is not a round element having only one outer surface such as a fiber optic cable.

According to a particularly preferred embodiment, the hard brittle material comprises glass. Furthermore, the element 1 is a glass ribbon 100. Glass ribbon 100 is moved in a direction along its longitudinal extension 101 by transport means 7, wherein the element 1 or specifically the glass ribbon passes through an arrangement of three rollers 4, 5, 6.

Now, apparatus 2 is intended to verify that the element 1 has a predefined breaking strength under tensile stress. For this purpose, the element is bent over rollers 4, 5, 6. Glass ribbon 100 is guided over rollers 4, 5, 6 in a manner so that the element 1 passes over a roller 4, 5, 6 at least once with each of its faces.

Specifically, glass ribbon 100 first runs over roller 4 with its face 11, then over roller 5 with the opposite face 10, then finally over roller 6 again with its face 11, whereby the glass ribbon is bent. The curvature of face 10 running over roller 5 is concave, that of the opposite face 11 is convex. The curvature of face 10 running over rollers 4 and 6 is convex, that of the opposite face 11 is concave. At the convex curvature a tensile stress is caused which is determined by the radius of curvature, while the face running over the roller surface 40, 50, 60 is subjected to a compressive stress in each case in the portion of the concave curvature. The latter is not critical and will not cause any breakage.

In order to move the glass ribbon 100 over the rollers 4, 5, 6, transport means 7 are provided. On the one hand, element 1 or glass ribbon 100 in the present case is advanced by the transport means 7, on the other hand a tensile force is exerted on the element 1 in the direction of advancement so that both faces 10, 11 are subjected to a tensile stress of at least 2 MPa. This tensile stress adds to the tensile stress caused by the bending over of the respective roller at the face 10, 11 facing away from the roller surface to define a resultant tensile stress. If a critical defect is present in element 1, the applied tensile stress will then cause breakage in the portion engaging on the surface of rollers 4, 5, 6. For monitoring and determining whether the element 1 has a defined breaking strength equal to the resulting tensile stress or whether the element 1 breaks under the applied resultant tensile stress, a monitoring means or device 24 is provided. The monitoring means or device 24 may be an appropriate sensor 13. The sensor 13 may, for example, be an optical sensor, in particular a camera which monitors the area of rollers 4, 5, 6. The additional tensile stress may even be substantially greater and may for example be at least 5 MPa, or even at least 10 MPa.

With the additional tensile stress exerted by transport means 7, the resultant maximum tensile stress can be accurately set to a desired value. Accordingly, a minimum stress resistance of the element 1 in the form of a tensile stress which the element should withstand can be predefined. This resultant tensile stress exceeds the tensile stress caused solely by the bending over rollers 4, 5, 6. Thus, the tensile force exerted on element 1 in the advancement direction and corresponding to a tensile stress of at least 2 MPa is then adjusted so that the resultant tensile stress is at least equal to the predefined minimum stress resistance. For example, if for a given glass thickness a tensile stress of 5 MPa is caused at the face facing away from the roller surface due to the rollers 4, 5, 6, but the element 1 is to be tested for a minimum stress resistance of 30 MPa, the transport means will exert an additional tensile stress of 5 MPa, optionally even higher.

According to one embodiment of the invention, the tensile force on element 1 is exerted by the pulling action of a conveyor belt 8 downstream of rollers 4, 5, 6 in the direction of advancement, on which the element 1 is adhering. In particular, element 1 might be adhered to conveyor belt 8 by suction. According to this embodiment of the invention, therefore, conveyor belt 8 is a vacuum conveyor belt. In order to establish a tensile force by the drive of conveyor belt 8, means for retaining the element 1 are utilized. A simple way to implement this is to provide a further conveyor belt 9 to which the element 1 is adhered. In particular, this further conveyor belt 9 may also be a vacuum conveyor belt.

Because of stress corrosion cracking, what is also important for the reliability of a statement as to whether the glass will withstand a specific tensile stress, in addition to the absolute magnitude of the tensile stress applied, is the duration of exposure to this stress. Without being limited to the specific implementation of the transport means, it is generally preferred for this purpose that the element 1 is passed over the rollers 4, 5, 6 at a rate in a range from 3 to 30 meters per minute.

For an element 1 that is being passed over the rollers this exposure duration further depends on the so-called wrap angle. This angle is the angle of the contact area of the respective roller 4, 5, 6 with the glass ribbon. In this respect, according to one embodiment of the invention it is contemplated that the distance of the rollers 4, 5, 6 and their height level relative to each other with respect to the longitudinal extension of the element 1 are selected so that the wrap angle which is the opening angle of the sector of the roller surface 40, 50, 60 along which the element 1 is in contact with the roller surface 40, 50, 60, is at least 10°. Particularly preferred is a wrap angle of at least 20°.

In the example shown in FIG. 1, the intermediate roller 5 is supported at a different level than the two outer rollers 4, 6. The greater the difference in height levels the longer the glass ribbon 100 is guided around the rollers 4, 5, 6 and consequently the greater the wrap angle. A similar effect is caused when the distance of rollers 4, 5, 6 is reduced.

Generally, without being limited to the particular arrangement of the rollers shown in FIG. 1, an arrangement with three rollers is preferred in which the element 1 passes over a first roller 4 with a first one 10 of its faces, then passes over an intermediate roller 5 with the opposite, second one 11 of its faces, and then passes over a last one 6 of the three rollers again with the first one 10 of its faces.

Figure 2:
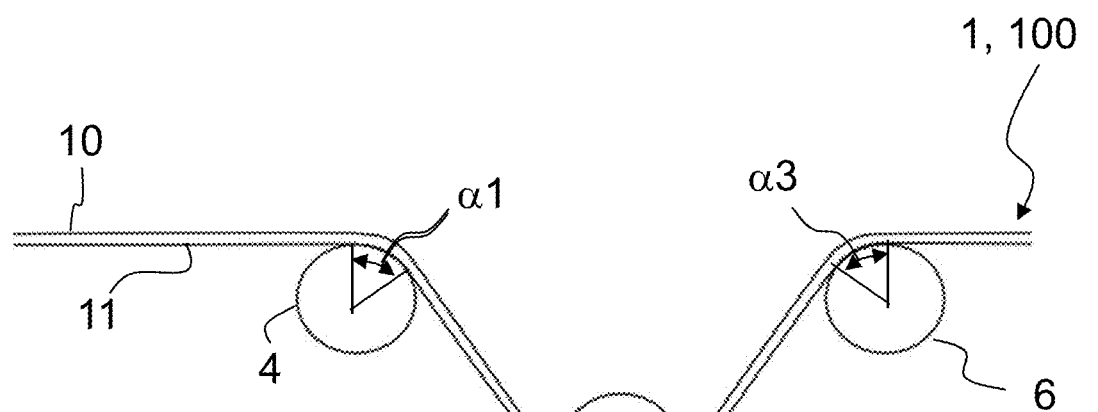
FIG. 2 is a side view of the rollers of the apparatus at a first level and distances of the rollers.
Figure 3:
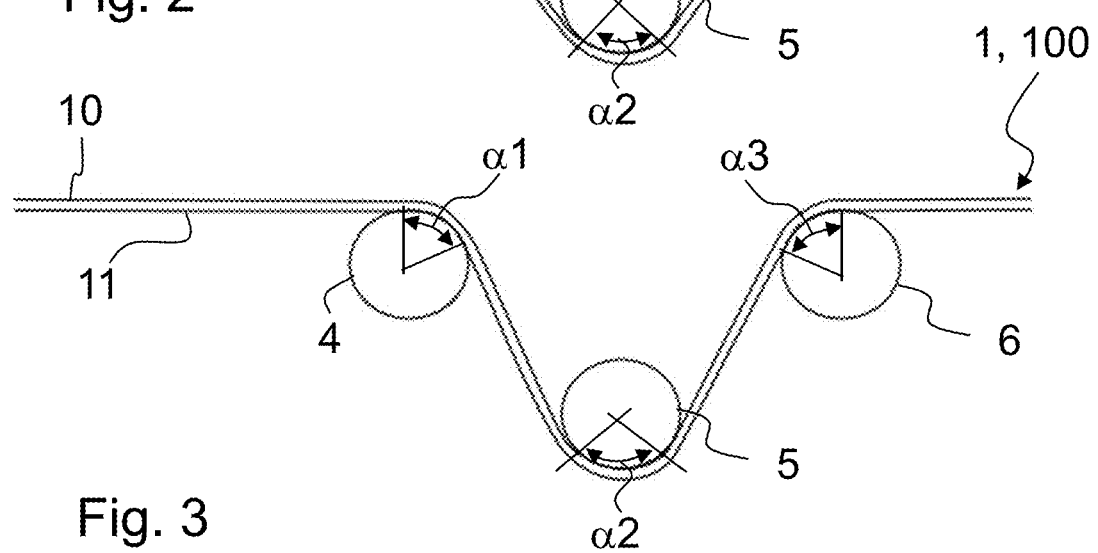
FIG. 3 is a side view of the rollers of the apparatus, at a different level and with different distances of the rollers.

This is illustrated by way of FIG. 2 and FIG. 3. These two figures show a side view of rollers 4, 5, 6 with the glass ribbon 100 guided thereover. Indicated are the wrap angles $\alpha 1$, $\alpha 2$, $\alpha 3$ on rollers 4, 5, 6. In FIG. 3, the distance between rollers 4, 5, 6 is reduced compared to the position in FIG. 2. The wrap angle is determined by the deflection angle of element 1 at the respective roller. The greater the deflection angle, the greater is the wrap angle. Since at the intermediate roller 5 deflection is twice that at the neighboring rollers 4, 6, the associated wrap angle $\alpha 2$ is accordingly greater than wrap angles $\alpha 1$, $\alpha 3$ at rollers 4, 6. If the intermediate roller 5 is further lowered or if the distance between rollers 4, 5, 6 is reduced as shown in FIG. 3, the wrap angles will increase. In the case of very thin glasses, the wrap angle largely depends on the arrangement of the rollers, since rigidity of the element 1 only plays a minor role here. If rigidity is neglected, the resulting wrap angle at rollers 4, 6 is 180° minus the deflection angle.

An arrangement with three rollers 4, 5, 6 may in particular be such that after having passed the last roller 6 the element 1 runs at the same level as when passing over the first roller 4. Accordingly, the first and last rollers 4, 6, are arranged so that their roller surfaces 40, 60 lie at the same level. The term 'same level' generally refers to the same position in a direction perpendicular to the advancement direction and perpendicular to the rotational axes of rollers 4, 6. Such an arrangement is advantageous, since the wrap angle can be adjusted by altering the position of the intermediate roller 5 or by altering the distance of the rollers without changing the position of element 1.

The following table lists wrap angles and tensile stresses for different amounts of lowering of the intermediate roller 5 and different roller diameters for such an arrangement with three rollers:

| No | Roller diameter [mm] | Glass thickness [μm] | Roller lowering [mm] | Max. tensile stress [MPa] | Wrap angle [°] |
|---|---|---|---|---|---|
| 1 | 160 | 50 | 100 | 25 | 19 |
| 2 | 160 | 50 | 150 | 25 | 33 |
| 3 | 160 | 50 | 200 | 25 | 44 |
| 4 | 160 | 50 | 250 | 25 | 53 |
| 5 | 160 | 50 | 300 | 25 | 63 |
| 6 | 160 | 100 | 100 | 47 | 7 |
| 7 | 160 | 100 | 150 | 50 | 23 |
| 8 | 160 | 100 | 200 | 50 | 34 |
| 9 | 160 | 100 | 250 | 50 | 44 |
| 10 | 160 | 100 | 300 | 50 | 56 |
| 11 | 80 | 50 | 100 | 40 | 6 |
| 12 | 80 | 50 | 150 | 50 | 22 |
| 13 | 80 | 50 | 200 | 50 | 35 |
| 14 | 80 | 50 | 250 | 50 | 46 |
| 15 | 80 | 50 | 300 | 50 | 54 |

The distance of the rollers from rotational axis to rotational axis was 500 millimeters in these exemplary embodiments. The glass of the thin glass ribbon is an alkali-free aluminosilicate glass of type AF32 having the following characteristics:

| Parameter | Value | Unit |
|---|---|---|
| Young's modulus: E | 74.8 | GPa |
| Poisson's ratio: ν | 0.238 | |
| Density: ρ | 2430 | kg/m$^3$ |

From a comparison of the examples it becomes apparent that the wrap angle may substantially decrease with increasing glass thickness and less lowering. In order to obtain a larger wrap angle greater than 20°, the intermediate roller may be lowered further, as is demonstrated by the significant difference between examples 6 and 10, as well as between 11 and 15.

More generally stated, in particular in case of rather large glass thickness, high rigidity, and/or slight roller lowering, a wrap angle greater than 0° is favorable so that a defined minimum bending radius is provided which is determined by the roller diameter. For reliably guiding the glass ribbon it is also advantageous if the ribbon not only contacts the roller along a straight line in parallel to the roller axis.

According to another embodiment, the course of the glass ribbon or more generally of the sheet-like element over the at least one roller may be determined using a spline function. For this purpose, at least one interpolation point, also known as knot, of the spline function is defined on each of the rollers. In particular a cubic spline is useful for this purpose. The spline function is created subject to the constraint that at the knots the surface of the element 1 made of hard brittle material extends tangentially to the surface of the deflection element.

Figure 4:
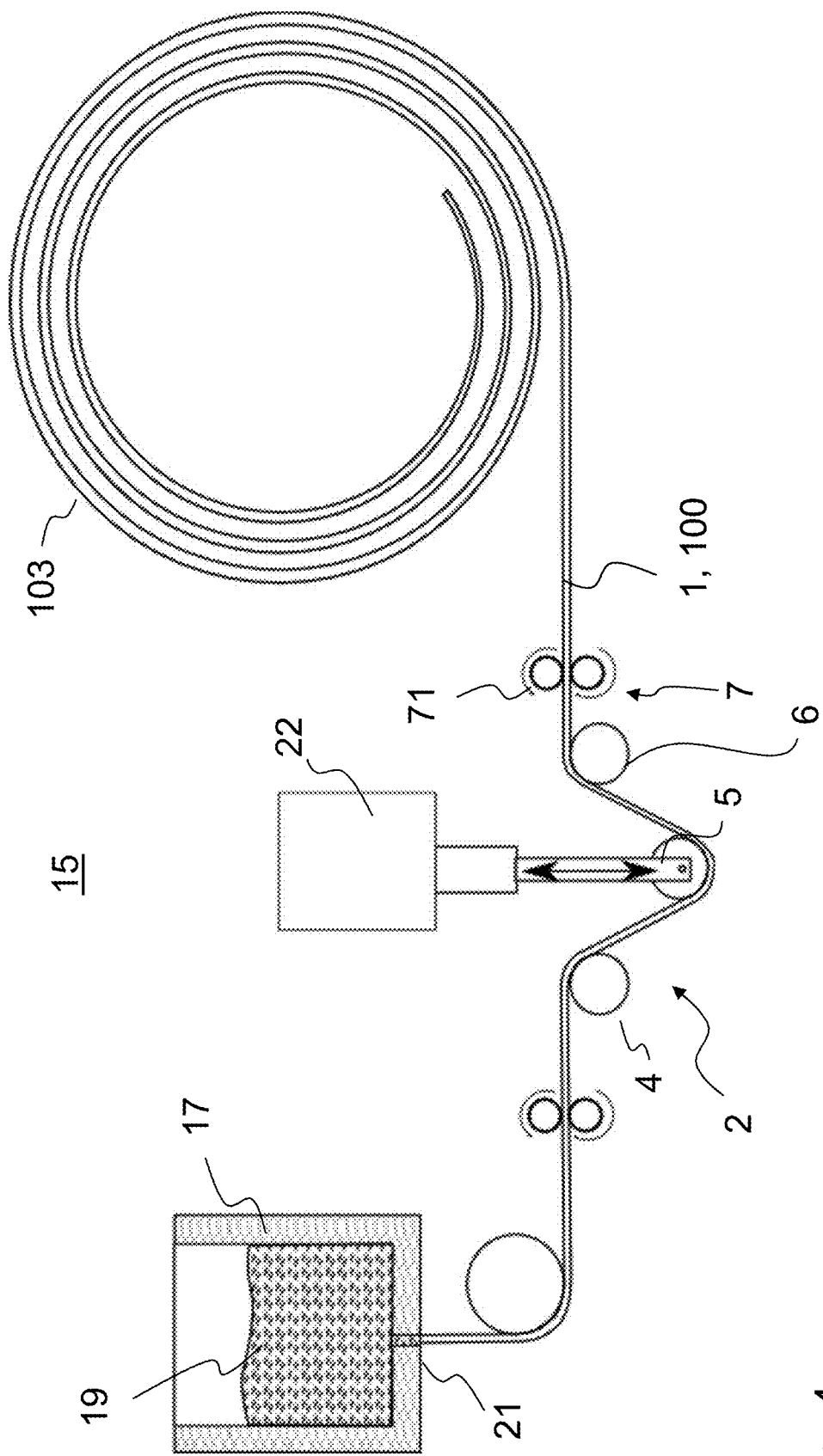
FIG. 4 shows a glass manufacturing system.

FIG. 4 shows a glass manufacturing system 15 including an apparatus 2 according to the invention. The glass manufacturing system comprises a melt container 17 containing molten glass 19. From molten glass 19, an element 1 is produced in the form of a glass ribbon 100 by drawing from a nozzle 21. The glass ribbon 100 is then passed over rollers 4, 5, 6 of the apparatus 2 for strength testing and is then wound up to form a roll 103. As described above, the value of the tensile stress to be verified, to which the glass ribbon 100 should withstand, is determined by the diameter of rollers 4, 5, 6 and the additional tensile stress exerted by transport means 7. In the illustrated arrangement, merely by way of example, no vacuum conveyor is employed for imparting the tensile stress, but a driven roller pair 71.

Without being limited to the particular example illustrated, according to one embodiment of the invention lifting means 22 may be provided by means of which the position of one or more of rollers 4, 5, 6 can be adjusted relative to the other rollers. This can be used to adjust the lowering of roller 5 with respect to the neighboring rollers 4, 6 and hence the wrap angle in the event of a change in glass thickness.

Figure 5:
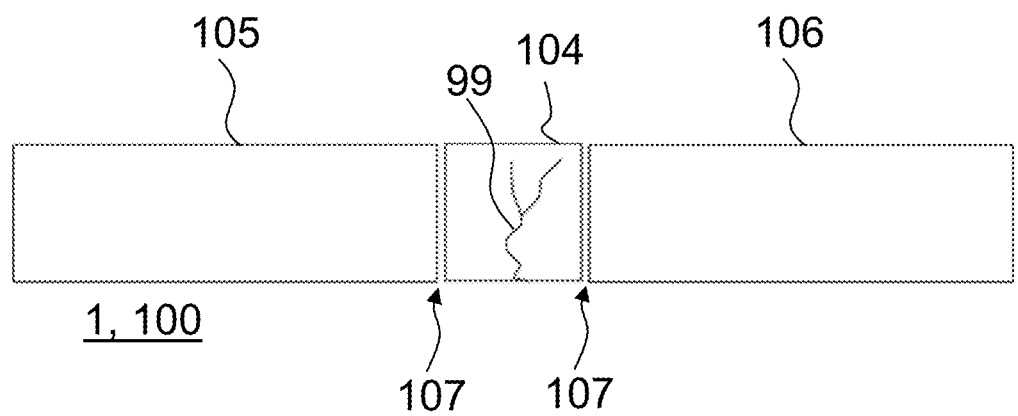
FIG. 5 shows a glass ribbon including a crack.

If the apparatus of the invention is used for testing large elements 1, such as a long glass ribbon 100 as in the illustrated example, and actually a fracture is caused by the stress, it is not necessary to discard the entire element 1 as defective. Rather, if a critical defect has caused a crack, according to one embodiment of the invention a portion including the crack may be separated and the remaining portions can be further processed. More particularly, in case it is detected that the glass ribbon 100 has broken under the resultant tensile stress applied, a portion of the glass ribbon 100 which includes the crack 99 may be separated. FIG. 5 shows a glass ribbon 100 having a crack 99, with portion 104 including the crack 99, and with the adjacent intact portions 105, 106 separated at separation points 107, which can be further processed. Further processing may comprise the winding into a roll 103 as shown in FIG. 4, for example.

The arrangement with three rollers 4, 5, 6 has another particular advantage which especially comes into play in the processing of glass ribbons 100.

Glass manufacturing processes often are continuous processes. For example, with the apparatus 2 shown in FIG. 4 a continuous glass ribbon 100 is produced. However, usually the glass ribbon 100 will be portioned, for example by being wound up into a glass roll 103 as illustrated. When the wound-up glass ribbon 103 has reached the desired length, the next glass roll can be prepared. But to this end the completed glass roll 103 has to be severed from the advancing glass ribbon 100 and the glass roll has to be removed. In such portioning steps it can be very advantageous if the glass ribbon 100 does not move further meanwhile. However, it would be very unfavorable to stop the drawing process. Such an interruption would result in considerable glass thickness variations, inter alia.

The apparatus 2 of the invention may now generally be used very beneficially in a continuous production process of an element 1 for retaining a portion of element 1 while another portion advances. For this purpose, a portion of element 1 downstream of rollers 4, 5, 6 as seen in the direction of advancement is retained, preferably by transport means 7, while a portion upstream of the rollers continues to move in the advancement direction, and this preferably at a constant rate. For this purpose, the position of at least one of rollers 4, 5, 6 is altered so that due to the change in position the length of the path of element 1 over rollers 4, 5, 6 increases, so that the advancement of the element upstream the retained portion of element 1 is absorbed. In the example shown in FIG. 4, the change in position can be easily realized at the intermediate roller 5 by lifting means 22. This will be explained below with reference to FIGS. 6 to 8 which show process steps for discharging a completed thin glass roll 103.

Figure 6:
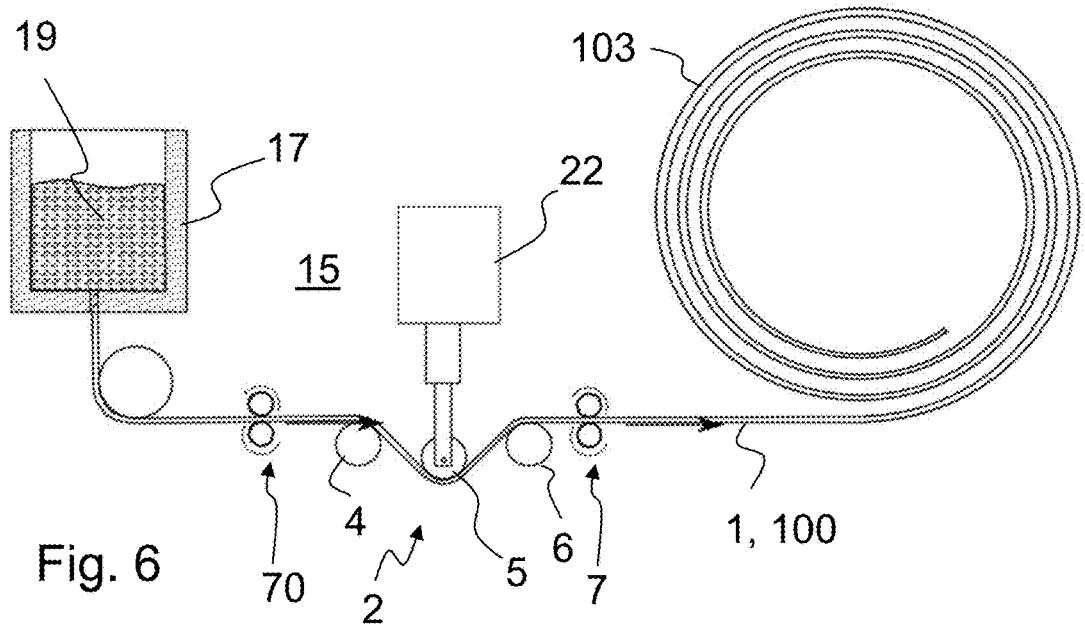
FIG. 6 illustrates method steps for discharging a completed thin glass roll.

First, as shown in FIG. 6, an element 1 in the form of a glass ribbon 100 is drawn from a melt 19, passed through apparatus 2 and wound up to form a thin glass roll 103. The intermediate roller 5 is at a position so that the glass ribbon 100 is little deflected.

When the glass ribbon 100 already wound into a thin glass roll 103 has the intended length, the thin glass roll 103 should be removed and a new thin glass roll should be started without stopping the drawing process.

Figure 7:
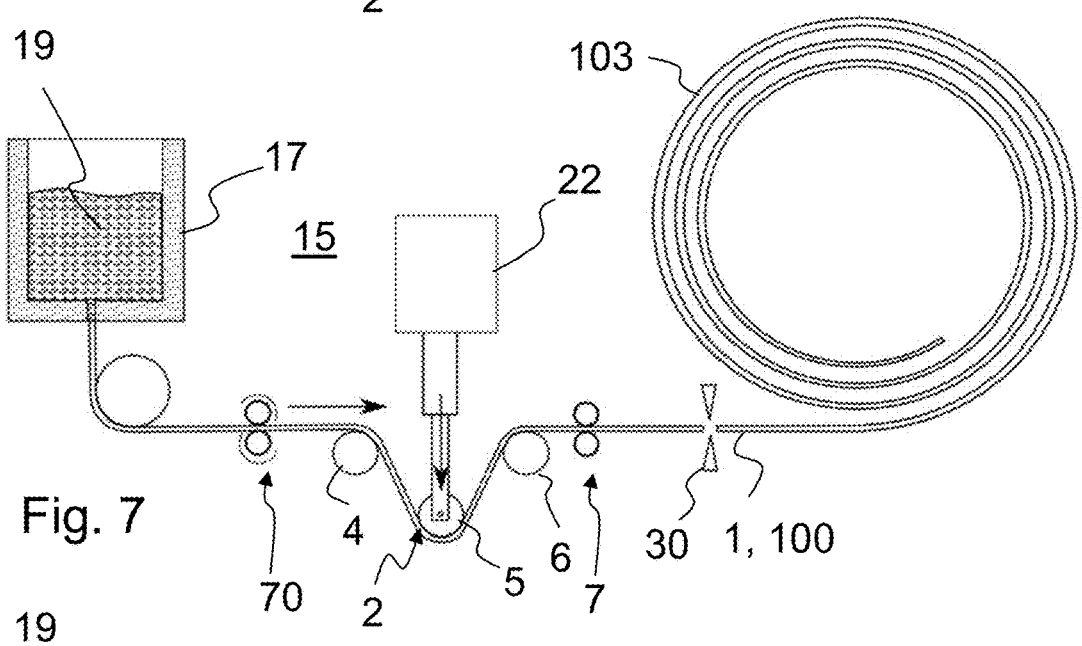
FIG. 7 illustrates method steps for discharging a completed thin glass roll.

As shown in FIG. 7, transport means 7 now stop the thin glass ribbon 100 and severing means 30 disposed downstream of transport means 7 or between transport means 7 and thin glass roll 103 separate the thin glass ribbon 100. Thin glass roll 103 can now be removed. While thin glass ribbon 100 is stopped by transport means 7, the thin glass ribbon is at the same time guided over rollers 4, 5, 6 in a manner so that the path length thereof is extended. This is preferably done continuously. With the extension, the advancement of thin glass ribbon 100 upstream of the point at which the ribbon is retained is absorbed.

In the illustrated example, the extension of the path is achieved by moving roller 5 by lifting means 22.

Figure 8:
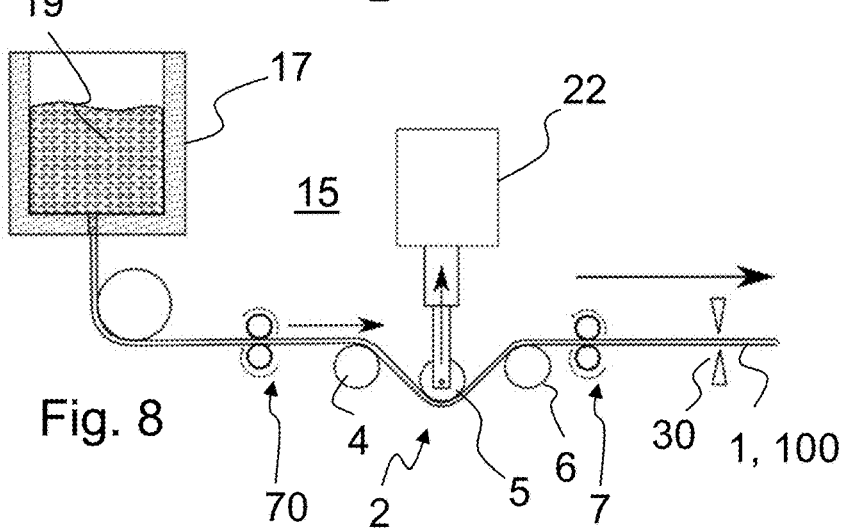
FIG. 8 illustrates method steps for discharging a completed thin glass roll.

Subsequently, as shown in FIG. 8, the thin glass ribbon 100 is again transported by transport means 7. Now, another thin glass roll may be produced, for example. At the same time, roller 5 is displaced so that the path of thin glass ribbon 100 trough rollers 4, 5, 6 is shortened. For this purpose, in the illustrated example roller 5 is returned into its initial position also shown in FIG. 6, by lifting means 22. With the shortening of the path a higher advancement rate is caused downstream of the arrangement of rollers 4, 5, 6, compared to the advancement rate at which the thin glass ribbon enters the roller arrangement. For example, when a thin glass roll is wound up, the winding speed will accordingly temporarily increase during the returning of roller 5.

Figure 9:
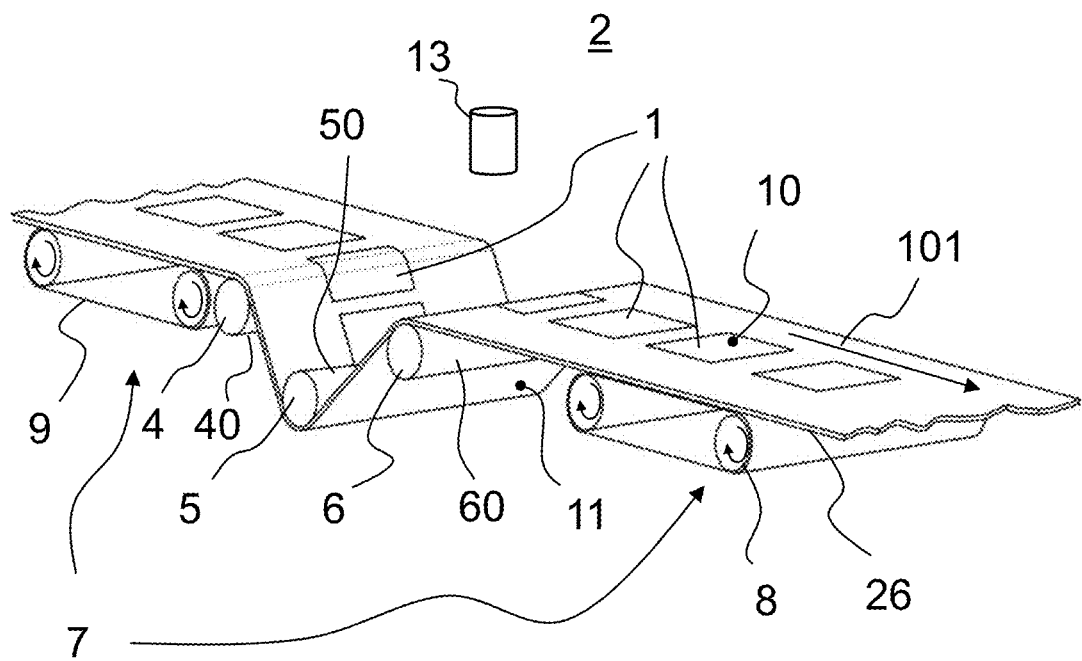
FIG. 9 shows a variant of the example shown in FIG. 1, with transportation of discrete sheet-like elements.

In the previous examples, the element 1 made of hard brittle material was a continuous thin glass ribbon 100. However, the invention can also be applied to discrete sheet-like elements 1. FIG. 9 shows an example. In this example, the discrete sheet-like elements 1 are conveyed by a belt 26 forming part of transport means 7. Belt 26 and thus the elements 1 placed on belt 26 are passed over rollers 4, 5, 6 so that the elements 1 are bent according to the diameter of rollers 4, 5, 6. In order to subject each of faces 10, 11 to a tensile stress, the belt may as well have a double-layered design, and in this case the elements 1 are inserted between the layers of belt 26. An additional tensile stress of at least 2 MPa may be exerted on elements 1 by providing the belt in stretchable form and fixing the elements on the belt, for example. When the belt is stretched, the force required therefor is then transferred to elements 1 as well.

The radii of rollers 4, 5, 6 and the additional tensile force in the advancement direction may generally be determined and matched based on statistical parameters that can be determined upon breakage of samples of the element 1. Particularly suitable for this purpose is the average breaking stress and the width of the frequency distribution at break. Both parameters can be converted from a mechanical tensile stress σ into corresponding bending radii R using the relationship $$R = \frac{E}{2\sigma} \cdot t. \tag{1}$$

In the above relationship E denotes the modulus of elasticity, also known as Young's modulus, of the material of the element, and t denotes the thickness thereof.

The width of the frequency distribution can be characterized by variable $$s = \sqrt{\frac{1}{N-1} \sum_{i=1}^{N} (R_i - \langle R \rangle)^2} \quad (2)$$

that corresponds to a standard deviation.

Here, N is the number of samples tested, $R_i$ is the bending radius corresponding to the breaking stress of the $i^{th}$ sample, and $\langle R \rangle$ is the bending radius corresponding to the average breaking stress. In case of a large or indeterminate number of samples or if the statistical characteristics of the material of element 1 are known, the standard deviation of the probability distribution of the breaking stress of the element can be used instead of variable s.

It has been found that a favorable range of diameters for rollers 4, 5, 6 is given by a range between $R_{min}$ and $R_{max}$, with the following applying for these radii:

$$R_{min} - \frac{E \cdot d}{2\sigma_T} = \langle R \rangle \cdot \left\{ 1 + \exp\left( \frac{s}{\langle R \rangle \cdot 0.053} - 2.9 \right) \right\} \text{ to} \quad (3)$$

$$R_{max} - \frac{E \cdot d}{2\sigma_T} = \langle R \rangle \cdot \left\{ 3.5 + \exp\left( \frac{s}{\langle R \rangle \cdot 0.051} - 2.3 \right) \right\}. \quad (4)$$

Here, E is Young's modulus, d is the thickness of element 1, and $\sigma_T$ is the tensile stress of at least 2 MPa additionally exerted on element 1 in the advancement direction. With the values for $R_{min}$ and $R_{max}$, a test method is provided with, on the one hand, a sufficient stress limited by $R_{min}$ and, on the other hand, a maximum value based on statistical parameters, which limits the breakage rate of element 1.

Accordingly, in a modification of the invention it is contemplated that the tensile stress $\sigma_T$ of at least 2 MPa exerted by the tensile force in the advancement direction and/or the radii of the rollers are selected (preferably by adapting the two parameters to each other) so that the element 1 is bent over rollers 4, 5, 6 with a bending radius which is within the range between $R_{min}$ and $R_{max}$ in accordance with the relationships given above.

Accordingly, this modification of the invention moreover provides an apparatus with at least one element 1 made of hard brittle material, comprising transport means 7 adapted to exert a tensile stress $\sigma_T$ of at least 2 MPa on the element 1, and rollers 4, 5, 6 having radii in the range from $R_{min}$ to $R_{max}$.

An apparatus that is particularly useful for determining statistical variables s and $\langle R \rangle$ of the element is disclosed in German patent application DE 10 2014 110 855 A1. The disclosure of this application with respect to the method and apparatus for determining variables s and $\langle R \rangle$ is fully incorporated into the subject matter of the present application by reference. The method for testing the breaking strength of sheet-like samples made of brittle-fracture material, in particular glass ribbons, generally comprises subjecting a first face of the samples to a tensile stress σ in a portion along the edge of the sample to be examined by pressing the sample in the portion to be examined against a template surface of a dimensionally stable template that has a defined curvature; so that the curvature of the template surface is imposed on the portion to be examined; wherein a template surface having a first bending radius R is used and the breaking strength of the sample is examined under the mechanical tensile stress σ corresponding to this bending radius R; and this test is repeated with successively reduced bending radius R and associated increased tensile stress σ until the sample breaks; and an analysis is performed to determine the tensile stress σ or bending radius at which the sample has broken.

It will now be described in more detail how the course of the sheet-like element over one or more rollers can be determined using a spline function, and how parameters of the occurring tensile stress can be derived therefrom.

One embodiment of the invention with respect to a description of the course of the sheet-like element generally comprises to determine or contribute to the determination of the actual minimum bending radius based on the calculated course, i.e. based on the spline function.

This embodiment may be implemented in the arrangement for strength testing according to the invention or may be performed with this arrangement, in particular for determining a current tensile stress which is determined by the position of the one or more rollers.

The method of determining the minimum bending radius based on a spline interpolation may most generally be used for a method of strength testing intended for documenting and verifying that the sheet-like element withstands the tensile stress exerted on the surface thereof, which is defined by the minimum bending radius.

Accordingly, in the method of the invention of strength testing it may be contemplated that the course of the sheet-like element 1 over the at least one roller is determined using a spline function, in particular a cubic spline, wherein at least one knot of the spline function is defined on each roller.

The minimum bending radius of the sheet-like element 1 may then be determined from the spline function.

In particular the tensile stress to which the faces 10, 11 are subjected by the bending and/or the tensile stress to which the faces 10, 11 are subjected by the tensile force in the advancement direction and/or the resultant tensile stress of these two tensile stresses may be determined from the minimum radius of curvature of a spline function, in particular of a cubic spline, between knots defined on the one or more roller surfaces 40, 50, 60.

Figure 10:
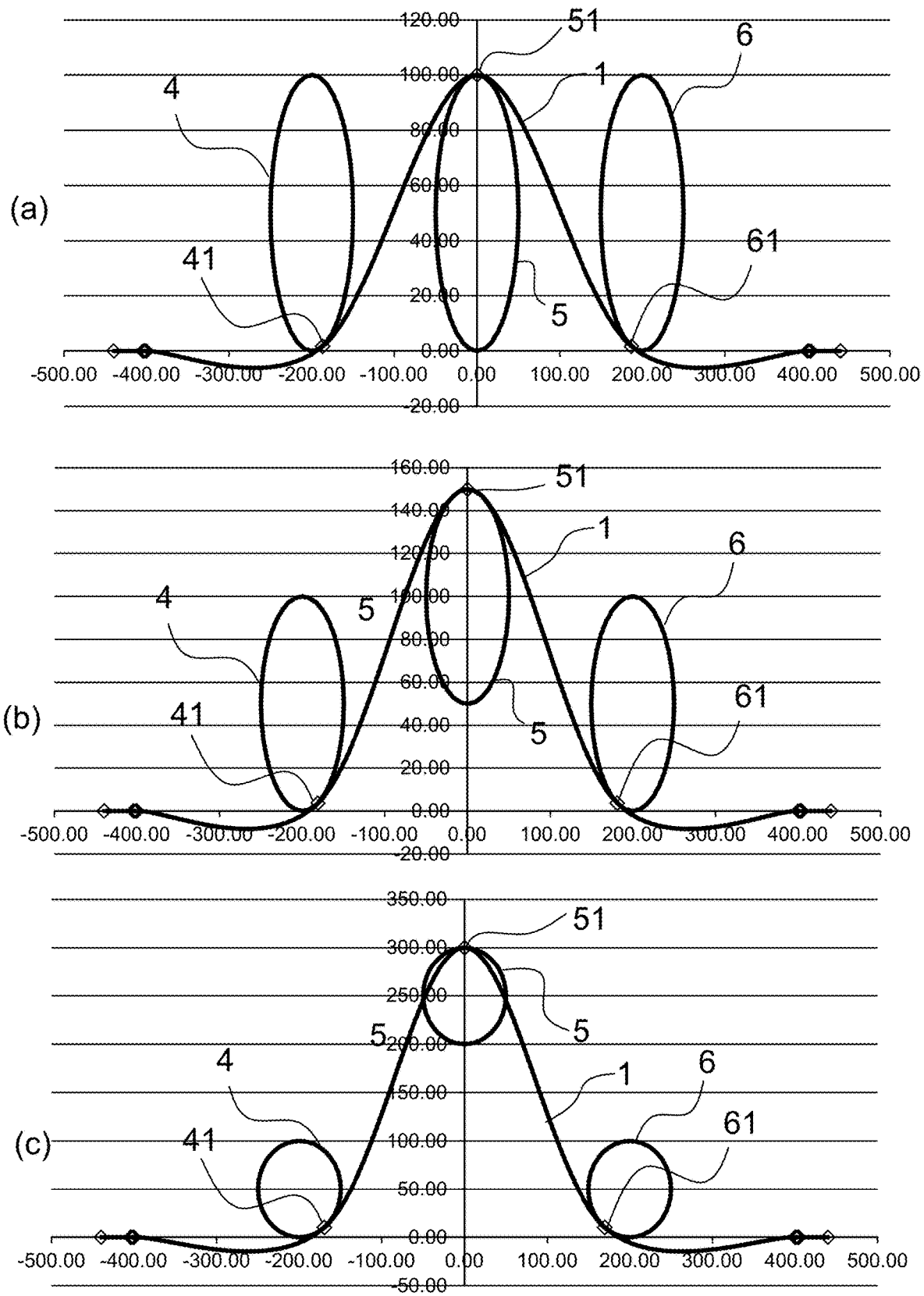
FIG. 10 shows three graphs with cubic spline functions which describe the course of a glass ribbon over three rollers.

FIG. 10 shows three graphs with spline functions, each of which represents the course of a sheet-like element 1, in particular a glass ribbon, over an arrangement comprising three rollers 4, 5, 6. In the graphs the rollers are represented by appropriate functions. Because of the different scales of the abscissa and ordinate, rollers 4, 5, 6 do not appear circular, but oval.

The spline function is defined by interpolation points, or knots, 41, 51, 61 on the rollers. Depending on the location of the intermediate roller 5, the cases as shown in graphs (a), (b), (c) are obtained. In the case of graph (a), the deflection is so small that the radius of curvature on roller 5 is greater than the radius of the roller. In the case of graph (b), roller radius of roller 5 and radius of curvature at knot 51 are matched. In graph (c), finally, for a single knot 51 the radius of curvature of element 1 is smaller than the radius of the roller at knot 51, due to the large deflection of roller 5 relative to rollers 4, 6. In this case, the course of element 1 can no longer be described by the three illustrated knots 41, 51, 61. Rather, a particular wrap angle is obtained. The element engages on the roller surface along the associated circular arc, such as shown in FIG. 2 and FIG. 3. In this case, the minimum radius of curvature of element 1 is then determined by the radius of the roller. In this case, in which the radius of curvature $R_E$ of the element 1 at a knot is smaller than the radius of curvature $R_W$ of the roller, $R_E < R_W$, a spline function correctly reflecting the course of element 1 over the roller with the respective knot (and also completely) may be determined as follows: In this case at least two knots are provided whose position on the surface of the roller is varied until the curvature radii of element 1 are sufficiently well matched with the curvature radius of the surface of the deflection element. The term "sufficiently well" again means with a deviation less than a predetermined threshold. The position of the knots may be quickly found using an interpolation method. For example the method of bisection is suitable. Bisection searches for the zero point of a suitable function by successive interval halving. In particular for this purpose, the zero point of the difference between radii of curvature $R_E - R_W$ may be easily sought.

In graph (c), however, the case that the minimum radius of curvature is determined by the curvature of the roller surface does not apply for rollers 4 and 6. Possibly, in case of only tangential engagement, the radius of curvature might be smaller than at the intermediate roller 5 here. As a result thereof, faces 10, 11 are then subjected to different tensile stresses. Therefore, the performed strength test will possibly not have the same informative value for both faces. Generally, without being limited to the specific illustrated examples, it is therefore contemplated according to a further embodiment of the invention that a spline function with knots on the one or more rollers is used to verify that the tensile stresses at the two faces 10, 11 are equal or at least differ by less than a predetermined threshold. More simply stated, the spline test is used to verify that the proof test is symmetric for predetermined positions of the deflection elements.

Now, with the knowledge about the course of element 1 acquired using the spline function, according to a refinement of this embodiment of the invention the position of the rollers can be altered so as to match the radii of curvature and therefore the tensile stresses exerted due to the deflection on the deflection elements. Thus, first it is checked using a spline function with knots on the rollers, whether the tensile stress is the same on both faces or at least differs by less than a predetermined threshold value, and for the case that the threshold is exceeded, the position of at least one of the rollers is altered in a manner so as to reduce the difference in tensile stress between the two faces 10, 11. Particularly suitable for this purpose is to reduce the distance between rollers 4 and 6.

LIST OF REFERENCE NUMERALS

1 Sheet-like element
2 Apparatus for testing the strength of 1
4, 5, 6 Roller
7, 70 Transport means
8, 9 Conveyor belt
10, 11 Faces of 1
13 Sensor
15 Glass manufacturing system
17 Melt container
19 Molten glass
21 Nozzle
22 Lifting means
24 Monitoring means
26 Belt
30 Severing means
40, 50, 60 Roller surface
71 Roller pair
99 Crack
100 Glass tape
101 Longitudinal extension of 100
103 Glass roll
104 Portion of 100 including a crack
105, 106 Intact portions of 100
107 Separation point

What is claimed is:

1. An apparatus for strength testing of a sheet element made of hard brittle material and having two opposite faces for a predefined breaking strength under tensile stress, the apparatus comprising:
   a transport device;
   at least two rollers operatively connected to the transport device, the transport device being adapted to pass the sheet element over the at least two rollers in a manner so that the sheet element is bent and each of the two opposite faces is subjected to a first tensile stress in a portion in which the opposite face is in contact with a surface of the at least two rollers;
   wherein the transport device is configured to exert a second tensile force on the sheet element in a advancement direction so that both of the two opposite faces are subjected to the second tensile stress of at least 2 MPa, wherein the second tensile stress and the first tensile stress add up to define a resultant tensile stress; and
   a sensor adapted to monitor the sheet element and to determine whether the sheet element has a defined breaking strength equal to the resultant tensile stress or whether the sheet element breaks under the resultant tensile stress.

2. The apparatus as claimed in claim 1, wherein the at least two rollers comprise an arrangement of three rollers arranged so that the sheet element passes over a first roller with a first one of the two opposite faces, then passes over an intermediate roller with the opposite, of the two opposite faces, and then passes over a last one of the three rollers again with the first one of the two opposite faces.

3. The apparatus as claimed in claim 1, further comprising lifting device configured to adjust a position of one or more of the three rollers relative to the other rollers.

4. An apparatus for strength testing of a sheet element made of hard brittle material and having two opposite faces for a predefined breaking strength under tensile stress, the apparatus comprising:
   a first roller having a first surface over which a first face of the sheet element passes;
   a second roller having a second surface over which a second face opposite to the first face of the sheet element passes, the first and second rollers being positioned with respect to each other so as to bend the sheet element in a first direction at the first roller so that a first tensile stress is induced in a second face opposite to the first face;
   a third roller having a third surface over which the first face of the sheet element passes, the second and third rollers being positioned with respect to each other so as to bend the sheet element in a second direction at the second roller so that a second tensile stress is induced in the first face
   a transport device configured to exert a tensile force on the sheet element to pull the sheet element through the first, second, and third rollers in an advancement direction so that both of the two opposite faces are subjected to the second tensile stress of at least 2 MPa, wherein the first and second tensile stresses add up to define a resultant tensile stress; and a sensor configured to determine whether the sheet element has a defined breaking strength equal to the resultant tensile stress or whether the sheet element breaks under the resultant tensile stress.

5. The apparatus as claimed in claim 4, wherein the transport device comprises a first conveyor belt arranged downstream, in the advancement direction, of the third roller.

6. The apparatus as claimed in claim 5, wherein the first conveyor belt is a first vacuum conveyor belt that uses suction to adhere the sheet element to the first conveyor belt.

7. The apparatus as claimed in claim 4, wherein the transport device comprises a driven roller pair arranged downstream, in the advancement direction, of the third roller.

8. The apparatus as claimed in claim 4, further comprising a second conveyor belt arranged upstream, in the advancement direction, of the first roller, wherein the second conveyor belt is configured to advance the sheet element through the first, second, and third rollers in the advancement direction.

9. The apparatus as claimed in claim 8, wherein the second conveyor belt is second vacuum conveyor belt that uses suction to adhere the sheet element to the second conveyor belt.

10. The apparatus as claimed in claim 4, wherein the sensor is an optical sensor configured to monitor an area of at least one of the first, second, and third rollers.

11. The apparatus as claimed in claim 4, further comprising a lifting device configured to adjust a position of at least one of the first, second, and third rollers.

12. The apparatus as claimed in claim 4, further comprising a lifting device configured to adjust a position of the second roller relative to the first and third rollers.

13. The apparatus as claimed in claim 11, wherein the first and third rollers lie at a same position in a direction perpendicular to the advancement direction and perpendicular to rotational axes of the first and third rollers.

14. The apparatus as claimed in claim 12, wherein the lifting device is configured to lengthen a path length through the first, second, and third rollers.

15. The apparatus as claimed in claim 14, wherein, during lengthening the path length, the lifting device is raised with respect to the first and third rollers while the transport device is stopped.

16. The apparatus as claimed in claim 15, further comprising a severing device positioned downstream, in the advancement direction, of the transport device.

* * * * *